(12) United States Patent
Vogele

(10) Patent No.: US 10,736,768 B2
(45) Date of Patent: Aug. 11, 2020

(54) DEVICE FOR IMMOBILIZATION

(71) Applicant: Michael Vogele, Schwabmünchen (DE)

(72) Inventor: Michael Vogele, Schwabmünchen (DE)

( * ) Notice: Subject to any disclaimer, the term of this patent is extended or adjusted under 35 U.S.C. 154(b) by 693 days.

(21) Appl. No.: 15/323,688

(22) PCT Filed: Jul. 3, 2015

(86) PCT No.: PCT/EP2015/001352
§ 371 (c)(1),
(2) Date: Apr. 21, 2017

(87) PCT Pub. No.: WO2016/000825
PCT Pub. Date: Jan. 7, 2016

(65) Prior Publication Data
US 2017/0246024 A1   Aug. 31, 2017

(30) Foreign Application Priority Data

Jul. 3, 2014  (DE) .................... 20 2014 005 396 U

(51) Int. Cl.
*A61F 5/37* (2006.01)
*A61B 6/04* (2006.01)
(Continued)

(52) U.S. Cl.
CPC .......... *A61F 5/3769* (2013.01); *A61B 6/0421* (2013.01); *A61B 90/39* (2016.02);
(Continued)

(58) Field of Classification Search
CPC .... A61F 5/3769; A61F 5/37; A61F 13/00051; A61F 13/00021; A61F 2013/00451;
(Continued)

(56) References Cited

U.S. PATENT DOCUMENTS 3,313,511 A * 4/1967 Koerner ............... A61B 6/0421
248/499
3,442,270 A * 5/1969 Steinman .......... A61F 13/00021
602/79
(Continued)

FOREIGN PATENT DOCUMENTS

DE      19640366 A1   12/1997
DE   102012100559 A1    7/2013
(Continued)

OTHER PUBLICATIONS

International Search Report (ISR) with patent family annex (German and English) and written opinion, dated Oct. 15, 2015, for PCT/EP2015/001352.

*Primary Examiner* — Tarla R Patel
(74) *Attorney, Agent, or Firm* — Myers Andras LLP; Joseph C. Andras

(57) ABSTRACT

In order to create a simple device for immobilizing the human body or parts of the body in a manner that is gentle on the patient, in particular for arranging medical targeting devices, markers or surgical instruments for image-guided, minimally invasive surgery, said device having at least one immobilization element (1) which can be positioned on the surface of the body, the immobilization element (1) is made of a bonded nonwoven fabric (2) which can be fastened by means of a micro hook-and-loop fastener (3).

17 Claims, 1 Drawing Sheet

(51) Int. Cl.
  *A61F 13/00* (2006.01)
  *A61B 90/00* (2016.01)
  *A61G 13/10* (2006.01)
  *A61G 13/12* (2006.01)
  *A61B 46/23* (2016.01)

(52) U.S. Cl.
  CPC .......... *A61F 5/37* (2013.01); *A61F 13/00021* (2013.01); *A61F 13/00051* (2013.01); *A61B 6/0492* (2013.01); *A61B 46/23* (2016.02); *A61B 2090/3983* (2016.02); *A61B 2090/3991* (2016.02); *A61F 2013/00412* (2013.01); *A61F 2013/00421* (2013.01); *A61F 2013/00451* (2013.01); *A61G 13/10* (2013.01); *A61G 13/12* (2013.01)

(58) Field of Classification Search
  CPC . A61F 2013/00421; A61F 2013/00412; A61B 90/39; A61B 6/0421; A61B 2090/3991; A61B 46/23; A61B 2090/3983; A61B 6/0492; A61G 13/12; A61G 13/10
  See application file for complete search history.

(56) References Cited

U.S. PATENT DOCUMENTS

| | | | |
|---|---|---|---|
| 3,982,132 A | | 9/1976 | Kay et al. |
| 4,039,705 A | * | 8/1977 | Douek ....................... C09J 4/06 428/41.5 |
| 4,067,565 A | * | 1/1978 | Daniels ................ A61B 6/0421 5/601 |
| 5,048,541 A | * | 9/1991 | Haneline .............. A61B 6/0421 128/830 |
| 5,329,934 A | * | 7/1994 | Bowman ................ A47D 13/08 128/870 |
| 5,800,346 A | * | 9/1998 | Adams ................... A61B 17/02 600/201 |
| 6,217,693 B1 | | 4/2001 | Pelham |
| 6,598,276 B2 | * | 7/2003 | Shepard ............. A44B 18/0011 26/51 |
| 2007/0235038 A1 | | 10/2007 | Alinsod et al. |
| 2010/0132412 A1 | | 6/2010 | Baldauf et al. |
| 2012/0266898 A1 | | 10/2012 | Vogele |
| 2017/0105877 A1 | * | 4/2017 | Buteux ............. A61F 13/00063 |

FOREIGN PATENT DOCUMENTS

| | | |
|---|---|---|
| DE | 102012211358 A1 | 1/2014 |
| WO | WO 9911452 A1 | 3/1999 |
| WO | WO 9933408 A1 | 8/1999 |

* cited by examiner

DEVICE FOR IMMOBILIZATION

BACKGROUND OF THE INVENTION

1. Field of the Invention

The invention relates to a device for immobilization according to the pre-characterizing features of claim 1. Here, in medical sense, "immobilization" means especially fixing, immobilizing, compression and/or positioning of the human body or human body parts (legs, arms), in particular also fixation of medical target devices, markers and/or surgical instruments for image-guided, minimally invasive surgical procedures, for which patients should be fixed.

2. Description of Related Art

In many areas of human medicine or medical research a secure fixation/immobilization or stabilization of the patient or body part of the patient or (mechanical) installation of equipment or appliances is necessary. This is very important in the field of diagnostic and therapeutic radiology, radiotherapy or operative/surgical procedures (e.g. neurosurgery), but also in pre- or post-operative care.

Implementing of computer technology in diagnosis and therapy demands on accuracy and repeatability are increased both in fixing a stereotactic frame system at humans and in the fixation of the body itself. Comfort, speed of application, mobility and costs play a significant role, wherein an invasive fixation (by screws etc.) should be avoided in any possible case.

So-called non-invasive fixation equipment is known as prior art:

a) Immobilization of the Body with Straps or Sleeves:

The patient's body lies on a foam pad and belts across the body fix the patient on this surface. Here, the disadvantage is that strong strain of the belts may cause pressure areas, offsets and skin swelling (inhomogeneous pressure distribution, in particular at the edges of taut bands or belts).

b) Fixation by Formwork:

Here, the patient is placed on a kind of "air mattress", which is filled with foam beads. By evacuating the air in the mattress, it is solidified by juxtaposing the foam beads. The vacuum mattress is adjusted in a first step and then further evacuated in a second step. The disadvantage is that the "mattress" commonly guarantees though restraint, but not an exact fixation. If the patient is uncooperative, sufficient immobilization is practically impossible. In addition, wrinkling or excessive pressing may often lead to pressure points and tissue injury, especially with anaesthetized patients.

c) Vacuum Fixation System:

In vacuum fixation systems, vacuum is applied to the body. By sucking the air at the patient's skin a good fixation may be created. Here, the disadvantage is that the vacuum pump has to run permanently. In addition, the vacuum system is relatively complex, so bad in handling and transport. In procedures requiring low sterility or even high sterility the air flow of the vacuum pump may cause a risk (germs). Further, high fixing forces are hardly possible because of long-lasting pressure injuries (e.g. hypoperfusion, bruising etc.) to occur. In case of failure of the vacuum, the fixation is abruptly lost, so that a risk to the patient may occur or the (surgical/radiological) intervention must be stopped or repeated.

Other techniques such as rails, plastic molding, plaster, etc. have similar drawbacks. In addition, these methods are still associated with considerable financial and time expenditure and are therefore used only for long-term applications.

Thus, the invention is based on the object to provide a device for fixing, which avoids the mentioned disadvantages, has a simple structure and is gentle to the patient on application. Moreover, the device should enable exact placement of calibration points (so-called markers) and/or target devices and/or other medical equipment (as instrument holders, MR coil (-s), etc.) and facilitate optimum access to operation areas.

This object is solved by an apparatus having the features of claim 1. Advantageous embodiments are subject of the dependent claims.

BRIEF SUMMARY OF THE INVENTION

An important feature is a consolidated non-woven fabric, enabling a stable fixing on the human body as the non-woven fleece engages directly with the hook side of a micro hook-and-loop fastener. The non-woven fabric is strengthened or consolidated by controlled stretching or pre-stretching winding on a roll, thus having a defined tensile strength to serve as counter element for such a micro hook fastener. Usually application of a hook-and-loop fastener has a symmetrical "double" of hook elements and counter-acting loop elements, but here the non-woven fabric forms the counter-acting loops for the hooks. The edge regions of the fabric strip are rather compliant, in contrast to stiff belts so that damage to the skin of the patient may be excluded. The more or less (cross-) elasticity of non-woven fleece perfectly adapts to the contour of the patient to allow optimal pressure distribution such that pressure peaks are avoided. Thus, the patient's body can be fixed in relation to a base plate of an examination or operating table and harmless compression of the body is achieved by applying slight pressure. As a side effect, this compression can also be used before, during and/or after the treatment, e.g. by inserting a wound compress between the fleece and a wound/surgery region, thereby forming a wound compression. Thus, unlike belts or bands with hook and loop fasteners, two cooperating hook and loop elements are no longer needed; rather, the consolidated non-woven fleece acts as one connecting element, and engages with the hooks of the one-sided micro hook fastener (in a releasable manner). Thus, cost of such a device for fixation of the human body or parts of the body is very low, since inexpensive, commercially available non-woven fleece forms a fastener-half that is a disposable product for each patient. In the manner of a bandage, the device is easy to use and the hygienic requirements are complied with. If necessary (e.g. for direct contact with the wound/the operational area), the fleece may be used in a sterile way.

The anchor element is preferably designed as a flexible foil with mushrooms and/or hooks as fasteners for the non-woven fleece. In this case, this foil is affixed as a strip with its back side (opposite to the hook side) on the side surface of a surgical table to serve as a stable anchorage. Such an anchor element is preferably made of polypropylene (PP) or polyamide (PA) so that it can be cleaned in a simple manner. The anchor element has relatively small (sub-millimeter) hooks, so that cleaning solutions are sucked-into the hook-side by capillary effect to cause a complete disinfecting of the anchor element. Classic VELCRO® or hook tapes do not have this property; they are not easy to disinfect and have, up to now, had a very limited use in hospitals—especially in the operating room or sterile areas with high hygienic requirements. The counter element of the inventive fixing member, namely the non-woven fleece, is usually configured as (sterile) disposable so that it can be easily disposed after skin contact, similar to a gauze bandage.

The non-woven fabric or fleece is mostly formed as a strip and can be used to create an access port as a surgical site to a body part (e.g. puncture opening) by perforations or regular cuts (e.g. of 1 cm diameter on each 10 cm length in the longitudinal direction). This allows one to place the non-woven fabric to the intended surgical site and then to fasten it on both ends. Alternatively, the non-woven fleece may have an oblong recess whose length is longer than the body spanning part of the non-woven fabric and the width of which is enough to perform an operation at a desired, exaggerated body part. The available mounting surface of the non-woven fabric is not reduced by the recess, such that the holding characteristics of the anchor element are not reduced. Here, the non-woven fleece is preferably unwound from a roll or coil and preferably cut to length, individually (e.g. with ordinary scissors etc.). However, the non-woven fabric may have pre-formed perforations, e.g. provided at each meter in length or greater distance (slightly longer than the width between the anchor elements) as desired separation points. The fleece strips may also overlap or be placed in several layers; thus, mechanical strain can be "individually" adjusted by each non-woven strip, whereby different parts of the body can be compressed to different extents and fixed. The advantage of multiple, overlapping and/or superposed fleece strips is also a safety aspect, as it is possible to ensure that the immobilization of the patient is not lost by dissolving one or more bands. In addition to the strip-like form it's also possible to design cloth or west-like versions of the non-woven fabric, having the advantage of even faster and simpler handling.

The consolidated non-woven fabric has high strength in tensioning direction (longitudinal direction of the strip) and lower strength or elasticity in the transverse direction (strip width) to conform perfectly to the patient's body. The fleece consolidation or strengthening can be carried out by various methods, as explained in WI KI PEDIA under "non-wovens", in particular by so-called needle fleeces. It is important that the non-woven fabric remains breathable and thus gentle on the patient. In addition, so-called markers and/or reinforcements may be integrated in the non-woven fabric.

As mentioned, the micro hook fastener or anchor element may be attached to the edge regions of an examination or operating table, in particular in movable form in profiles along the edges or bonded at the table. In this case standard profiles can be used, such as used for operating tables, examination tables, CT or MRI tables, etc. In addition, the anchor elements can be provided in the form of patches with adhesive strips or attached to fixation accessories (head shell, vacuum pads etc.) or glued thereto. Such fixing members can also include an additional device, in particular a marker or target device, preferably attached by at least one adapter plate which may have hook-like fasteners or an adhesive layer, as well. Thus, even the outer or top side of the non-woven fabric can be used for anchoring, too.

After fixing and sterile covering a surgical intervention (possibly with robot support) can be performed in an operating window, wherein the above-cited markers for imaging or surgical navigation are reproducibly mounted. As the non-woven fabric provide to a large-scale, ergonomic fixing, high holding forces are generated with maximum comfort. The adhesive forces can be further increased if a skin-friendly adhesive spray or a thin, double-sided tape applied to the non-woven fabric in the contact region facing the patient. Further, soft human tissue can be fixed, e.g. to keep it away from radiation beams.

BRIEF DESCRIPTION OF THE SEVERAL VIEWS OF THE DRAWINGS

Embodiments are described with reference to the drawing. The figures show in.

DETAILED DESCRIPTION OF THE PREFERRED EMBODIMENTS

Figure 1:
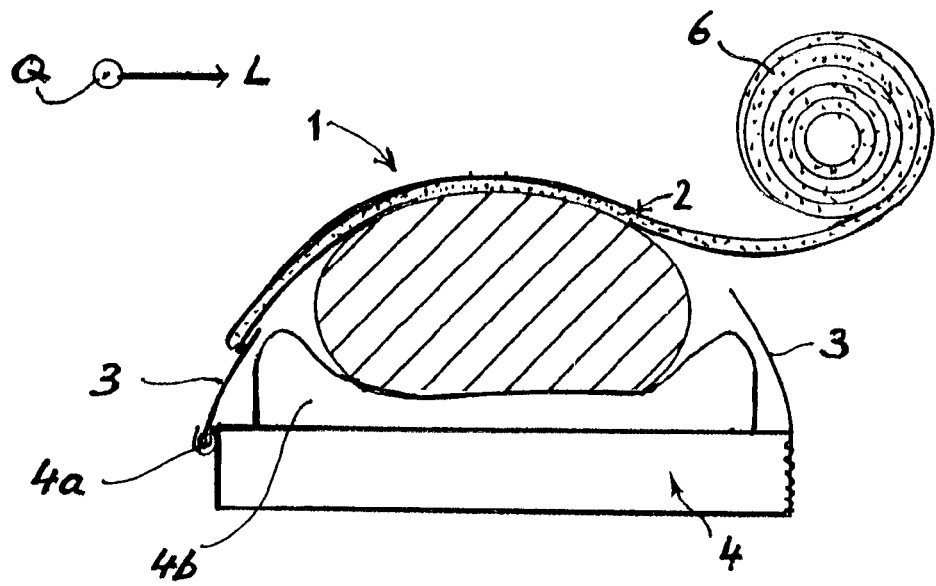
FIG. 1 shows the attachment of a device for immobilization.

The device for immobilization or fixation of the human body or of body parts consists of at least one fixing element 1 on the body (shown in hatched lines, here for example, a cross section of a human back resting on a cushion pad 4b) (FIG. 1). This positioning is done with a consolidated non-woven fabric 2, aka fleece, which is applied to the skin and tensioned to the left and right of the pad 4b to be fixed to a respective anchor element 3 (by engaging to the micro hooks 3a that are in the micrometer range, according to the designation "micro"). The non-woven fabric 2 preferably has a strip-like design and is especially wound on a coil or roll 6. The non-woven fleece 2 has high tensile strength in its mounting direction L (usually transverse to the longitudinal axis of the body), but is relatively elastic in the transverse direction Q thereof. An adapter plate 5a may be attached to the outside of the elastic fleece element or fixing element 1 in order to anchor a marker 5 (or other accessories) in a stable and reproducible manner (see FIG. 3). As shown on the left side of FIG. 1, the fixing element 1 is preferably attached to a base plate of an examination or operating table 4 via at least one profile 4a, e.g. a rounded groove guide. Some of these fixing elements 1 can be located along the human back, with distance from one another, such that several corresponding operation areas are formed between the multiple fixing elements 1.

Figure 2:
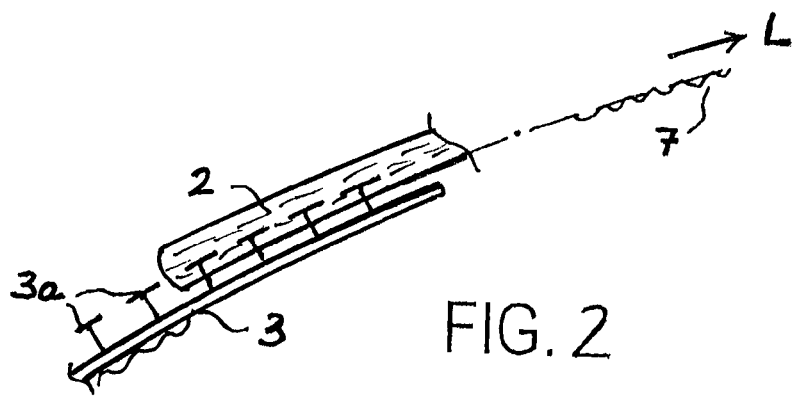
FIG. 2 is an enlarged detailed view of the connection on the left side of FIG. 1.

FIG. 2 is a greatly enlarged view of the connection between the non-woven fabric or fleece 2 and the anchor element 3 on the left side of FIG. 1, wherein plural T-formed hooks 3a in the micrometer range, (small mushroom or hook shape of these fasteners 3a is applicable, as well) engage with the fibers of the non-woven fabric 2, like claws. As also shown in FIG. 1, right side, a second anchor element 3 can be bonded to the right side of the operating table 4 (lateral to the patient) in the manner of an adhering tape to be adhered. Likewise, such a "patch" can be glued to the side of the patient support 4b, depending on the position of the fixated body part, e.g. in the shoulder area and/or the hips and/or in the leg area, etc. The fibers of the non-woven fabric 2 are mainly directed in the longitudinal direction L, thus ensuring high tensile strength. The right side of FIG. 2 indicates an adhesive layer 7 next to the anchor element 3 (i.e. towards the patient) to be preferably applied as by spraying shortly before fixing. This adhesive layer 7 can increase the sticking or immobilization forces or keep way soft tissue from of the surgical area (cf. access port or opening 2a in FIG. 3).

Figure 3:
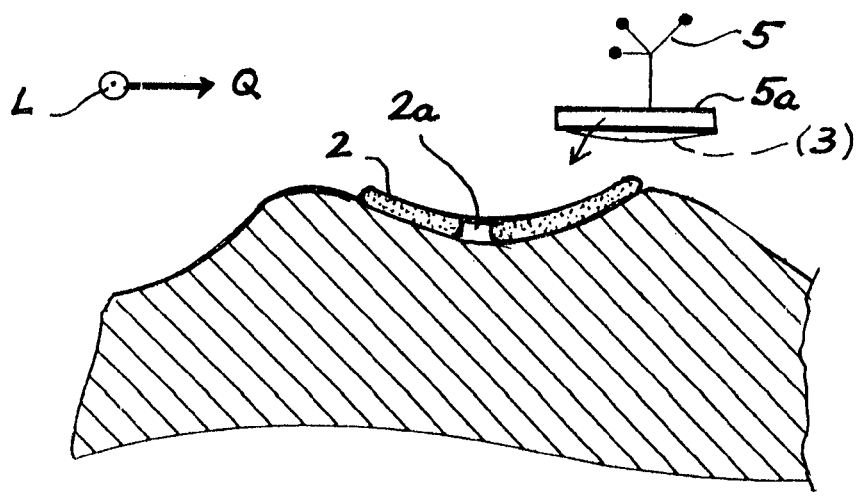
FIG. 3 shows the setting-up/fitting of additional devices such as an access opening 2a and a target device and/or marker 5.

As shown in FIG. 3 in cross section, such an opening 2a is provided for a puncture in the lumbar region (and in the strip-like non-woven fabric 2). Thus, the treating physician or medical person can fix any region of the body (whole human body or just body parts) as required. This results in universal adapting to operating tables and a simple fixing of surgical equipment and markers. It's also possible to add pads below the non-woven fabric 2 (to increasing comfort), wherein the non-woven fabric 2 enables the skin to "breathe", in contrast to conventional bands or collars, such that even prolonged use will not cause irritation. To sum up, body parts are immobilized with a defined pressure and at very low cost, wherein the proposed device can also be used with a device based on adhesive forces (cf. Applicant's DE 20 2011 005 573). This principle of micro hook-and-loop fasteners 3, wherein the loops are formed by the non-woven fleece 2 can also apply for fixing the above-mentioned adapter plate 5*a*, as indicated in FIG. 3. The underside of the adapter plate 5*a* can also be provided with an anchor element (i.e. the half of micro hooks) to be anchored on the outside ("loops") of the strained or tensioned non-woven fabric 2. The non-woven fleece 2 may also cross above and over the adapter plate 5*a* for additional fixation. This also applies to other medical accessories, such as MR coils or pressure sensors for detecting (respiratory) patient motion, which are securely fixed by the non-woven fabric 2 close to the body (like a second skin).

The invention claimed is:

1. A device for immobilization of the human body or of body parts, in particular for attachment of medical target devices, markers or surgical instruments for image-guided, minimally invasive surgery, with at least one fixing element (1) to be positioned on the body surface, characterized in that
the fixing element (1) comprises a consolidated non-woven fabric (2) which has at least two sides thereof fastened to and tensioned between a separate anchor element having micro hooks (3), the consolidated non-woven fabric forming the counter-acting loops for the micro hooks of the anchor element (3), characterized in that the non-woven fabric (2) has high tensile strength in the longitudinal direction (L) and is formed resilient in the transverse direction (Q).

2. The device according to claim 1, characterized in that the anchor element (3) has a flexible film with micro hooks (3*a*) in the form of mushrooms or hooks for engagement with the non-woven fabric (2).

3. The device according to claim 1, characterized in that the anchor element (3) is made of polypropylene (PP) or polyamide (PA).

4. The device according to claim 1, characterized in that the non-woven fabric (2) is a strip or cloth, in particular with at least one access opening (2*a*) to a body part.

5. The device according to claim 1, characterized in that the non-woven fabric (2) can be unwound from a roll (6), preferably to be cut to length at perforations.

6. The device according to claim 1, characterized in that the separate anchor element (3) having micro hooks is formed as a multi-use article and the non-woven fabric (2) is formed as a sterile disposable article.

7. The device according to claim 1, characterized in that the anchor element (3) is fastened at edge regions of an examination or operating table (4), in particular in profiles (4*a*) along the edges in moveable manner, or is adhered to the table (4) and/or a patient support (4*b*).

8. The device according to claim 1, characterized in that at least one additional device, in particular a target device (5) or elements for imaging can be fixed to the fixing element (1), preferably by means of at least one adapter plate (5*a*), which also carries hook-like connecting elements (3*a*).

9. The device according to claim 1, characterized in that an adhesive layer (7) is applied to the non-woven fleece (2), in particular in the form of a skin-compatible spray adhesive or thin double-sided adhesive tape.

10. The device according to claim 1, characterized in that the anchor element (3) is provided in the form of patches with adhesive strips or attached to fixation accessories, in particular to a head shell or a vacuum pad or glued thereto.

11. The device according to claim 1, characterized in that the anchor element (3) is provided at the underside of an adapter plate (5*a*).

12. A patient stabilization system for immobilization of a patient's body or body parts relative to a patient support table for a medical imaging procedure, comprising:
at least one anchor element (3) fastened to the patient support table, the anchor element comprising micro hooks for releasably engaging with counter-acting loops; and
an elastic fleece element (1) comprised of a consolidated non-woven fleece (2) that is stretchy in at least one direction for tensioning, and which natively forms counter-acting loops on both sides thereof for directly and releasably engaging the micro hooks of said at least one anchor element (3), the elastic fleece element stretched and tensioned over a body surface of the patient's body or body parts with an underside thereof releasably engaged with said at least one anchor element to apply immobilization forces to the patient's body or body parts for the medical imaging procedure by adapting to the contour of and gently compressing the patient's body or body parts toward the patient support table, characterized in that the non-woven fabric (2) has high tensile strength in the longitudinal direction (L) and is formed resilient in the transverse direction (Q).

13. The patient stabilization system of claim 12, characterized in that the consolidated non-woven fleece (2) is unwound from a roll (6) and cut to length.

14. The patient stabilization system of claim 12 wherein the anchor element is fastened at an edge region of the patient support table via an adapter plate that slides in a groove (4*a*).

15. The patient stabilization system of claim 12 wherein the anchor element is fastened at an edge region of the patient support table with an adhering tape.

16. The patient stabilization system of claim 12, further comprising:
a marker for use during the medical imaging procedure comprising a target device (5) and an adapter plate (5*a*) which carries hook-like connecting elements (3*a*) for releasably engaging with counter-acting loops;
the elastic fleece element (1) natively forming counter-acting loops on a topside thereof for directly and releasably engaging the hook-like connecting elements (3*a*) of said marker's adapter plate (5*a*); and
the marker releasably attached to the elastic fleece element (1).

17. The patient stabilization system of claim 12, characterized in that at least one access opening (2*a*) is cut into the elastic fleece element (1) to provide direct access to the patient's skin, the access opening being positioned as desired when the elastic fleece element is stretched and tensioned over a body surface of the patient's body or body parts.

* * * * *